US00PP15486P3

(12) United States Plant Patent
Boeder

(10) Patent No.: US PP15,486 P3
(45) Date of Patent: Jan. 25, 2005

(54) ***CHRYSANTHEMUM* PLANT NAMED 'ABBA'**

(50) Latin Name: *Chrysanthemum moriflorum*
Varietal Denomination: Abba

(75) Inventor: Mark Roland Boeder, Den Haag (NL)

(73) Assignee: Cleangro LTD (GB)

( * ) Notice: Subject to any disclaimer, the term of this patent is extended or adjusted under 35 U.S.C. 154(b) by 15 days.

(21) Appl. No.: 10/622,679

(22) Filed: Jul. 17, 2003

(65) Prior Publication Data

US 2004/0128727 P1 Jul. 1, 2004

Related U.S. Application Data

(60) Provisional application No. 60/396,828, filed on Jul. 17, 2002.

(51) Int. Cl.[7] ..... A01H 5/00
(52) U.S. Cl. ..... Plt./286
(58) Field of Search ..... Plt./286

(56) References Cited

U.S. PATENT DOCUMENTS

PP14,155 P3 * 9/2003 Noodelijk ..... Plt./286

OTHER PUBLICATIONS

*Chrysanthemum* Breeder's Association (CBA) Cataogue 2000 excerpt listing the *Chrysanthemum* variety 'Scott.'*

*Chrysanthemum* Breeder's Association (CBA) Cataogue 2001 listing the *Chrysanthemum* variety 'Scott.' See pp. 16 and 19 (color photograph).*

*Chrysanthemum* Breeder's Association (CBA) Cataogue 2002 excerpt listing the *Chrysanthemum* variety 'Scott.'*

*Chrysanthemum* Breeder's ASsociation (CBA) Cataogue 2003 listing the *Chrysanthemum* variety 'Scott.' See pp. 17 and 18 (color photograph).*

* cited by examiner

*Primary Examiner*—Anne Marie Grunberg
*Assistant Examiner*—Annette H Para
(74) *Attorney, Agent, or Firm*—Howrey Simon Arnold & White, LLP

(57) ABSTRACT

A new variety of *Chrysanthemum* plant named 'Abba' having a uniform canopy of dark pink single spoon flowers with a yellow/green disc. The new variety has a medium height and a free branching and uniform spreading habit with good foliage presentation.

1 Drawing Sheet

Latin name of the genus and species: Botanical classification: *Chrysanthemum moriflorum.*

Variety denomination: The new *Chrysanthemum* variety denomination is 'Abba.'

BACKGROUND OF THE INVENTION

The present invention comprises a new and distinct cultivar of *Chrysanthemum* botanically known as *Chrysanthemum moriflorum* and referred to by the cultivar name 'Abba'. 'Abba,' identified as 211750 originated from a cross made in a controlled breeding program at Chichester, West Sussex, United Kingdom.

The female parent of the new variety is an undistributed, unpatented seedling identified as P371D4. The male parent of the new variety is an undistributed, unpatented seedling identified as 15 P381D4. The new variety 'Abba' has been asexually reproduced by vegetative cuttings in Chichester, West Sussex, United Kingdom and the distinguishing characteristics are retained through successive generations of asexual reproduction.

BRIEF SUMMARY OF THE INVENTION

'Abba' is a pot type of *Chrysanthemum* plant variety having dark pink straight single spoon flowers.

Comparison with Female Parent

Plants of the new *Chrysanthemum* variety 'Abba' are dissimilar to the parent cultivar 'P371D4' in plant habitat and growth rate. In side-by-side comparisons in Chichester, West Sussex, United Kingdom, under commercial practice, plants of the new *Chrysanthemum* variety 'Abba' differed from plants of the parent cultivar 'P371D4' in the following characteristics.

1. The new variety 'Abba' produces dark pink single spoon flowers whereas the parent cultivar 'P371D4' produces pink single flowers.
2. Plants of the new variety 'Abba' have larger inflorescence than plants of the parent cultivar 'P371D4.'

Comparison with Male Parent

Plants of the new *Chrysanthemum* variety 'Abba' are dissimilar to the male parent 'P3811D4' in plant habitat and growth rate. In side-by-side comparisons in Chichester, West Sussex, United Kingdom, under commercial practice, plants of the new *Chrysanthemum* variety 'Abba' differed from plants of the parent 'P381D4' in the following characteristics.

1. The new variety 'Abba' produces dark pink single spoon flowers whereas the parent 'P381D4' produces white single flowers.
2. Plants of the new variety 'Abba' have larger and taller inflorescence than plants of the parent 'P381D4'.

Comparison with Other Varieties

Plants of the new *Chrysanthemum* variety 'Abba' are similar to the cultivar 'Scott' (U.S. Plant Pat. No. 14,155) in plant habitat and growth rate. However, in side-by-side comparisons in Chichester, West Sussex, United Kingdom, under commercial practice, plants of the new *Chrysanthemum* variety 'Abba' compared to plants of the cultivar 'Scott' in the following characteristics:

1. The new variety 'Abba' produces dark pink single spoon flowers whereas the cultivar 'Scott' produces purple single spoon flowers.
2. Plants of the new variety 'Abba' have larger and taller inflorescence than plants of the cultivar 'Scott.'

BRIEF DESCRIPTION OF ILLUSTRATIONS

Typical specimens of the plant and flowers for the new *Chrysanthemum* variety 'Abba' are shown in the accompanying digital photograph. The colors shown are as true as possible within the usual limits of this kind of illustration.

FIG. 1 is a whole plant view of the new variety 'Abba' grown in a pot. The plant shown in the illustration and described here is 53 days from commencement of Short Days.

DETAILED BOTANICAL DESCRIPTION

The following description of the new *Chrysanthemum* variety 'Abba' is of plants grown in a greenhouse in Chichester, West Sussex, United Kingdom in the month of February. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 18° C. at night and about 24° C. to 25° C. during the day under light conditions of about 5000 to 6000 foot candles. The plants respond well to the use of growth retardant, such as B9 treatment. To produce a commercial product the plants may be pinched once with the center bud removed. The typical container size for commercial growth is 14 cm. It has been observed that the shelf life of the new variety is about 24 days with a response time of about 8 weeks. The new variety is suitable for growth in a temperature range of 17° C. to 28° C.

The following description is with respect to a plant produced as pot *Chrysanthemum*. In the description of this new *Chrysanthemum* variety, color values have been taken from The Royal Horticultural Society Colour Chart (R.H.S.C.C.).

Plant

Plant type: Pot.
Habit: Upright and free branching.
Height: 25 cm.
Width: 32 cm.
Branching characteristics: Upright and free branching.
Length of lateral branches: 6–11 cm.
Number of breaks from pinch: 3–5.
Stem color: 137C.
Response time: 54.
Vigor: Medium.
Shelf life: 24 days.
Disease/pest (susceptibility/resistance observed): None observed to date.
Growth retardant type and treatment: 3 applications of 2.5 gm/liter B9 @ 2, 21 and 28 days after sticking of unrooted cuttings.

The plants were grown for 3 weeks in Long Day conditions (20 hours of light) and then transferred to Short Day conditions (13 hours of dark).

Propagation:
*Type.*—Vegetative Propagation Via Stem Cuttings.
*Time to rooting.*—12–14 days with soil temperatures of 18° C.
*Rooting habit.*—Fine and Fibrous.

Foliage

Number of leaves per lateral branch: 8–10.
Compound or single: Single.
Arrangement of leaves: Alternate.
*Shape of leaf.*—Typically 5 lobed ovate.
*Size of leaf.*—Width (cm): 4–6 cm. Length (cm): 6–10 cm.
*Leaf apex.*—Acute.
*Base.*—Acute.
*Attachment.*—Petioled.
*Aspect.*—Slightly Undulating.
*Margin.*—Palmetely Lobed.
*Surface characteristics.*—Top: Slightly pubescent. Bottom: Pubescent.
Petiole:
*Color.*—137A. Length: 1.25 cm.
Venation: Net prominent midvein at underside.
*Color.*—Upper side: Near 137B. under side: Near 138B.
Color:
*Mature leaf, upper side.*—Near 147A; under side: Near 138A.
*Young leaf, upper side.*—Near 137A; under side: Near 138B.

Flower

Flower appearance: Matte.
Flower type: Single.
Flower form: Cupped.
Flower shape: Circular.
Flowering habit: Cyme.
Number of blossoms per branch: 3–5.
Inflorescence form: Pyramidal.
*Depth of fully expanded blossoms.*—2 cm.
*Diameter of fully expanded blossoms.*—6 cm.
Sepals:
*Number.*—25–30.
*Outer color.*—Near 137C.
*Length.*—0.5–1 cm.
*Width.*—0.2 cm.
*Texture/appearance.*—Pubescent.
Peduncle: Peduncle length is shortest at the terminal flower and progressively longer moving down the stem.
*Length.*—3–9 cm, average 5 cm.
*Color.*—Near 137C.
*Surface.*—Pubescent.
*Habit.*—Slightly Curving.
*Strength.*—Medium.
Pedicel:
*Length.*—Terminal: 2–4 cm; lateral 3–6 cm.
*Color.*—Near 137C.
*Surface.*—Pubescent.

*Habit.*—Slightly curving.
*Strength.*—Medium.

Ray florets:
*Form/shape.*—Spatulate.
*Texture/appearance.*—Matte.
*Number per flower.*—35.
*Length.*—2–4 cm; Width: 0.2–0.5 cm.
*Apex.*—Rounded.
*Base.*—Tubular.
*Margin.*—Entire.

Disc florets:
*Form/shape.*—Cylindrical.
*Texture/appearance.*—Shiny.
*Number per flower.*—200–450.
*Length.*—0.6–0.9 cm; Width: 0.1 cm.
*Diameter of disc.*—1 to 2 cm.

Fragrance: Faint.

Flower bud (at onset of color):
*Length.*—1.5 cm.
*Diameter.*—1 cm.
*Form/shape.*—Globular.

General flower color:
1. *Ray florets, upper side.*—Immature: Near 63A. Mature: Near 63B. Older/Fading: Near 63C.
2. *Ray florets, under side.*—Immature: Near 76B. Mature: Near 76C. Older/Fading: Near 76D.
3. *Disc florets.*—Immature: Near 143B. Mature: Near 151B. Older/Fading: Near 151C.
4. *Bud.*—137A.

Flower progression with age: Flower form does not change with age but there is a slight color fading.

Reproductive Organs

Ray florets: Gynoecium present on Ray and Disc Florets.
*Pistil number.*—>30.
*Stigma color.*—Near 6C.
*Stigma shape.*—Forked.
*Style color.*—Near 6D.
*Style length.*—0.5 cm.

Disc florets:
*Pistil number.*—>25.
*Stigma color.*—Near 6C.
*Stigma shape.*—Forked.
*Style color.*—Near 6D.
*Style length.*—0.4 cm.

Androecium present on disc florets only:
*Stamen number.*—10.
*Anther shape.*—Thread.
*Anther color.*—Near 13B.
*Pollen color.*—Near 13B.
*Pollen quantity.*—Little.

Fruit and seeds: None observed to date.

What is claimed is:

1. A new and distinct variety of *Chrysanthemum* plant, substantially as described and illustrated herein.

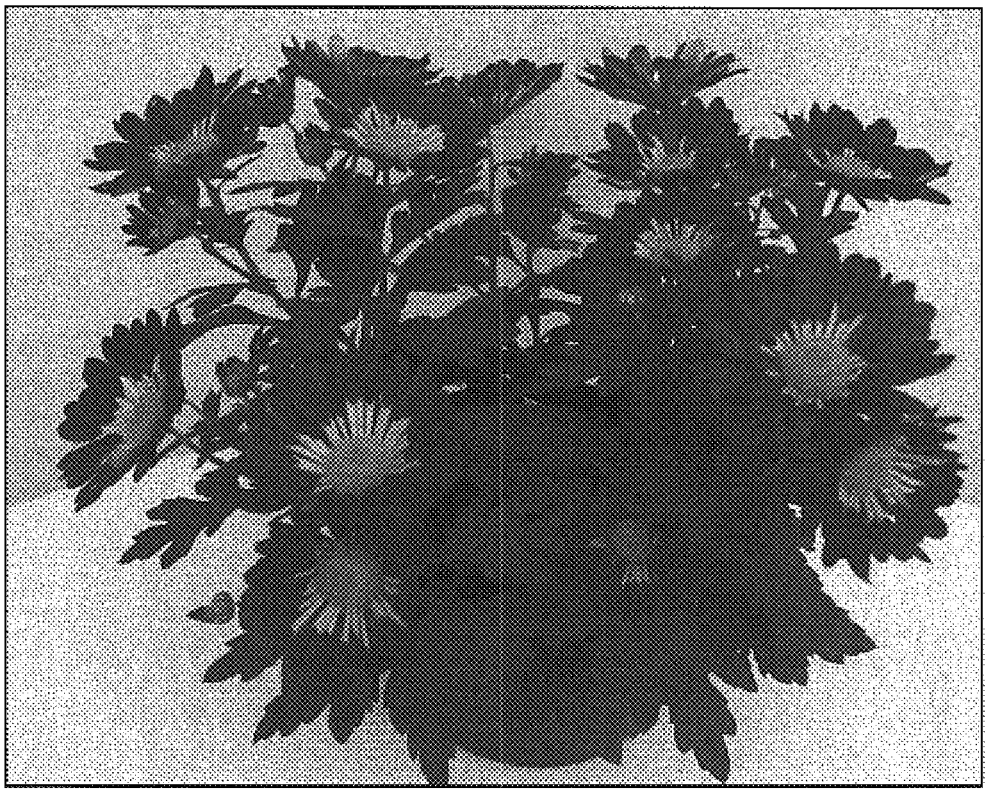

* * * * *